(12) United States Patent
Kim et al.

(10) Patent No.: US 11,213,451 B2
(45) Date of Patent: Jan. 4, 2022

(54) MASK HAVING MASSAGE FUNCTION AND MASK SYSTEM INCLUDING SAME

(71) Applicant: HUMACCOS CO., LTD., Seoul (KR)

(72) Inventors: Dong Hwan Kim, Seoul (KR); Tae Sik Shon, Namyangju-si (KR)

(73) Assignee: HUMACCOS CO., LTD., Seoul (KR)

(*) Notice: Subject to any disclaimer, the term of this patent is extended or adjusted under 35 U.S.C. 154(b) by 335 days.

(21) Appl. No.: 16/348,493

(22) PCT Filed: Nov. 6, 2017

(86) PCT No.: PCT/KR2017/012464
§ 371 (c)(1),
(2) Date: May 8, 2019

(87) PCT Pub. No.: WO2018/088763
PCT Pub. Date: May 17, 2018

(65) Prior Publication Data
US 2020/0060923 A1 Feb. 27, 2020

(30) Foreign Application Priority Data
Nov. 9, 2016 (KR) .......................... 10-2016-0148549

(51) Int. Cl.
*A61H 7/00* (2006.01)
*A45D 44/00* (2006.01)
(Continued)

(52) U.S. Cl.
CPC ........... *A61H 7/002* (2013.01); *A45D 44/002* (2013.01); *A45D 44/02* (2013.01); *A45D 44/22* (2013.01);
(Continued)

(58) Field of Classification Search
CPC .......... A61H 7/00; A61H 7/002; A61H 7/004; A61H 2201/105; A61H 2205/022; A45D 44/002; A45D 44/02; A45D 44/22
See application file for complete search history.

(56) References Cited

U.S. PATENT DOCUMENTS 4,052,981 A * 10/1977 Bachmann ......... A61H 23/0263
601/71
7,376,460 B2 5/2008 Bernabei
(Continued)

FOREIGN PATENT DOCUMENTS

CN 1121804 A 5/1996
CN 2514835 Y 10/2002
(Continued)

OTHER PUBLICATIONS

Korean Patent Application No. 10-2016-0148549, Notice of Allowance dated Sep. 26, 2017, 3 pages.

*Primary Examiner* — Samchuan C Yao
*Assistant Examiner* — Cana A Gallegos

(57) ABSTRACT

The present invention relates to a mask having a massage function and a mask system including the same. According to the present invention, the mask having the massage function comprises: a mask body; and a massage unit coupled to the mask body, wherein the massage unit includes: a massage pad; and a pad driving part for allowing the massage pad to move in one direction while pressing the skin of a user.

8 Claims, 13 Drawing Sheets

(51) Int. Cl.
*A45D 44/02* (2006.01)
*A45D 44/22* (2006.01)
*A61H 15/00* (2006.01)
*A61N 5/06* (2006.01)

(52) U.S. Cl.
CPC ....... *A61H 15/0078* (2013.01); *A61N 5/0616* (2013.01); *A61H 2201/105* (2013.01); *A61H 2201/1215* (2013.01); *A61H 2201/1652* (2013.01); *A61H 2205/022* (2013.01); *A61N 2005/0651* (2013.01)

(56) References Cited

U.S. PATENT DOCUMENTS

| | | | |
|---|---|---|---|
| 2004/0139981 A1 | 7/2004 | Liu | |
| 2005/0049528 A1* | 3/2005 | Lagercrantz | A61H 7/005 601/87 |
| 2006/0287615 A1* | 12/2006 | Yu | A61H 39/002 601/15 |
| 2007/0016269 A1 | 1/2007 | Suzuki | |
| 2009/0254014 A1* | 10/2009 | Son | A61H 9/0078 601/134 |
| 2012/0172951 A1* | 7/2012 | Choi | A61N 5/0616 607/91 |
| 2014/0142472 A1 | 5/2014 | Giraud et al. | |
| 2014/0350442 A1 | 11/2014 | Park et al. | |
| 2017/0181924 A1* | 6/2017 | Thorpe | A61H 7/002 |

FOREIGN PATENT DOCUMENTS

| | | |
|---|---|---|
| CN | 103919675 A | 7/2014 |
| CN | 204671751 U | 9/2015 |
| CN | 105267015 A | 1/2016 |
| DE | 3828565 C1 | 7/1989 |
| DE | 4116836 A1 | 11/1992 |
| JP | U54-049791 | 9/1977 |
| JP | H08317946 A | 12/1996 |
| JP | 2000014729 A | 1/2000 |
| JP | 2007020593 A | 2/2007 |
| JP | 2007037657 A | 2/2007 |
| JP | 2013-520221 A | 6/2013 |
| JP | 2015-501158 A | 1/2015 |
| JP | 2015-535457 A | 12/2015 |
| JP | 2017127370 A | 7/2017 |
| KR | 19980087763 A | 12/1998 |
| KR | 20-0185058 Y1 | 6/2000 |
| KR | 20040103601 A | 12/2004 |
| KR | 20-0412600 Y1 | 3/2006 |
| KR | 20070053408 A | 5/2007 |
| KR | 20120019928 A | 3/2012 |
| KR | 2020130001342 U | 2/2013 |
| KR | 101442627 B1 | 9/2014 |
| KR | 101530165 B1 | 6/2015 |
| KR | 20160126237 A | 11/2016 |
| WO | 2011/102594 A | 8/2011 |

\* cited by examiner

MASK HAVING MASSAGE FUNCTION AND MASK SYSTEM INCLUDING SAME

CROSS-REFERENCE TO RELATED APPLICATIONS

This application is a national stage of International Application No. PCT/KR2017/012464, filed 6 Nov. 2017, which claims the benefit of priority to Korean Application No. 10-2016-0148549, filed 9 Nov. 2016 in the Korean Intellectual Property Office, the disclosures of which are incorporated herein by reference.

TECHNICAL FIELD

The present invention relates to a mask having a massage function and a mask system including the same.

BACKGROUND ART

A mask is used to manage a user's skin by attaching it on the user's face, and various functional materials can be used to enhance the effect.

Conventional masks managed the skin by chemical action such as moisturizing, but it was difficult for the user to intuitively feel the effect of using the mask because there was no physical action such as massage.

Particularly, the conventional masks had no function for wrinkles of a face, and it was difficult for the user to feel that the skin condition of a specific area was improved.

DISCLOSURE

Technical Problem

Therefore, an object of the present invention is to provide a mask having a massage function and a mask system including the same.

Technical Solution

Objects of the present invention can be achieved by providing a mask having a massage function, including: a mask body; and a massage unit coupled to the mask body, wherein the massage unit includes: a massage pad; and a pad driving part for allowing the massage pad to move in one direction while pressing a skin of a user.

The massage pad may move in one direction while directly contacting the skin of the user.

The pad driving part may move the massage pad in an endless track manner.

The pad driving part may include: a belt configured to have the massage pad attached thereon; a roller connected to the belt; and a motor configured to rotate the roller.

The massage unit may further include a cosmetic supply unit to supply cosmetics to the massage pad.

The cosmetic supply unit may be formed of materials including a porous material, and the cosmetics may be discharged from the cosmetic supply unit by a contact between the massage pad and the cosmetic supply unit, to thereby be moved to the massage pad.

The mask may further include a cosmetic channel configured to receive cosmetics from an external side, wherein the cosmetic supply unit receives the cosmetics through the cosmetic channel.

The massage unit may further include a light emitting diode (LED) configured to irradiate light to the skin of the user.

The massage pad may massage the skin in a direction of from a center of the user's face toward a periphery of the user's face.

The mask may further include: a fixing unit configured to be attached to the mask body and closely fix the mask body to the user's face.

Objects of the present invention can also be achieved by providing a mask system having a massage function, including: a mask; a cosmetic container containing cosmetics; and a pump configured to supply the cosmetics to the mask, wherein the mask includes: a mask body; a massage unit coupled to the mask body; and a cosmetic channel configured to supply the cosmetics to the massage unit, wherein the massage unit includes a massage pad configured to be moved in one direction while pressing a skin of a user.

Advantageous Effects

According to the present invention, a mask having a massage function and a mask system including the same is provided.

MODE FOR INVENTION

The present invention will be described in more detail with reference to the drawings.

The accompanying drawings, which are included to provide a further understanding of the technical concept of the present invention, are incorporated in and constitute a part of the specification, and are not intended to limit the scope of the present invention. Also, the attached drawings may be exaggerated in size and spacing in order to explain the relationship between the respective components.

A mask system according to a first embodiment of the present invention will be described with reference to FIGS. 1 to 7.

Figure 1:
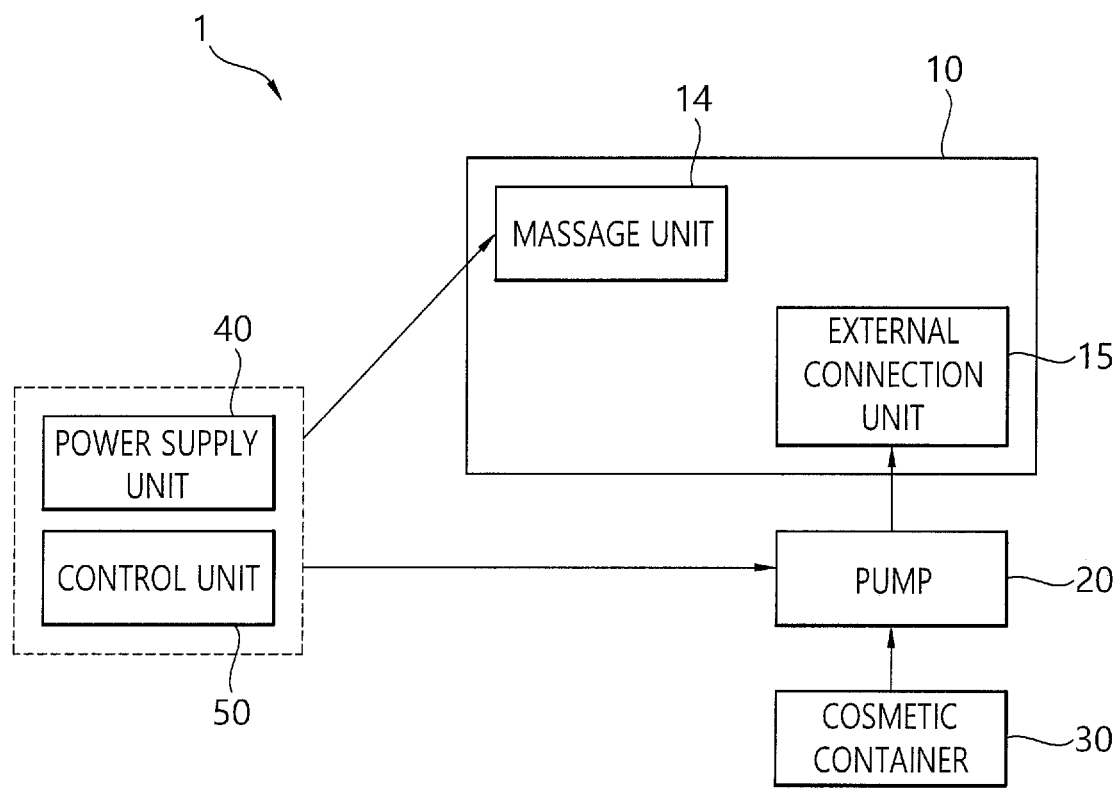
FIG. 1 shows the construction of a mask system according to a first embodiment of the present invention.
Figure 2:
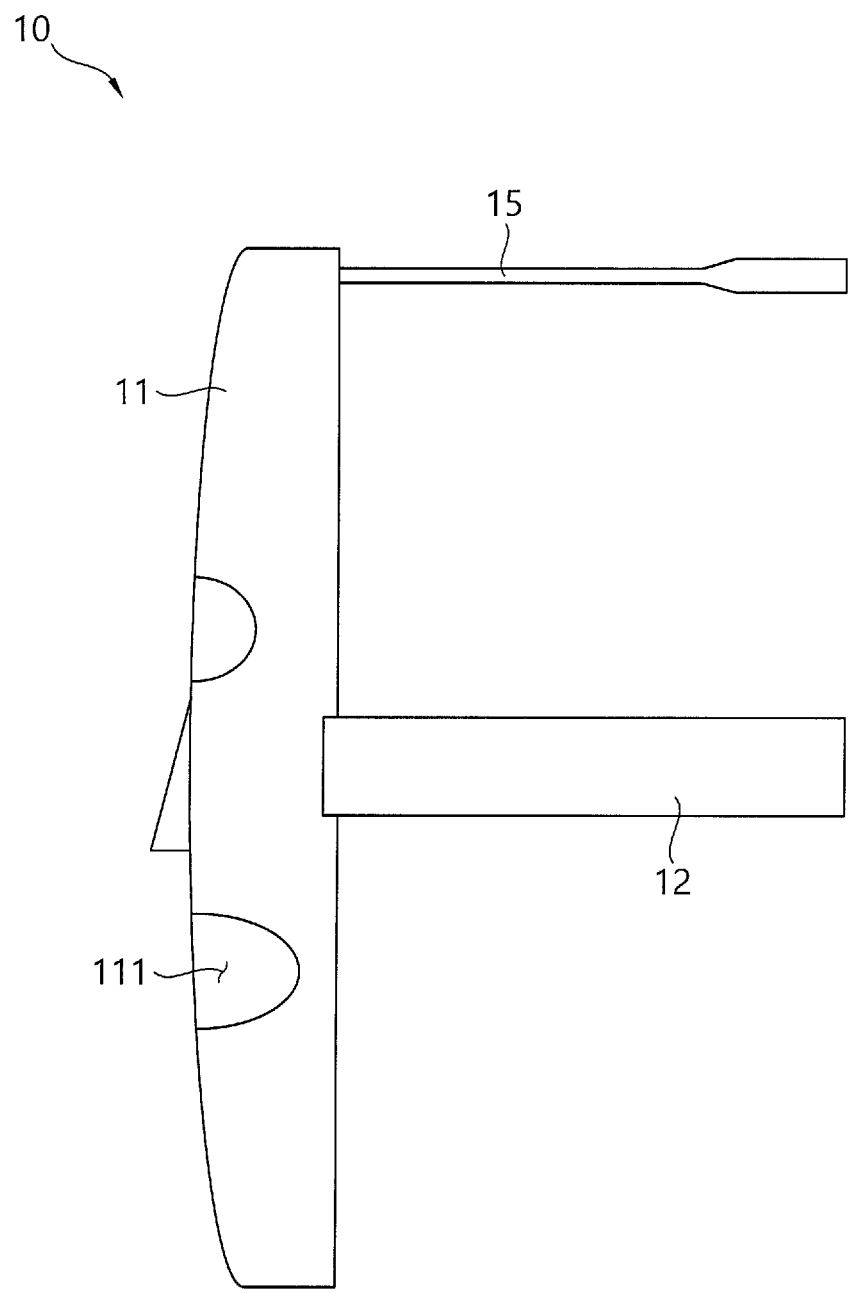
FIG. 2 is a side view of the mask according to the first embodiment of the present invention.
Figure 3:
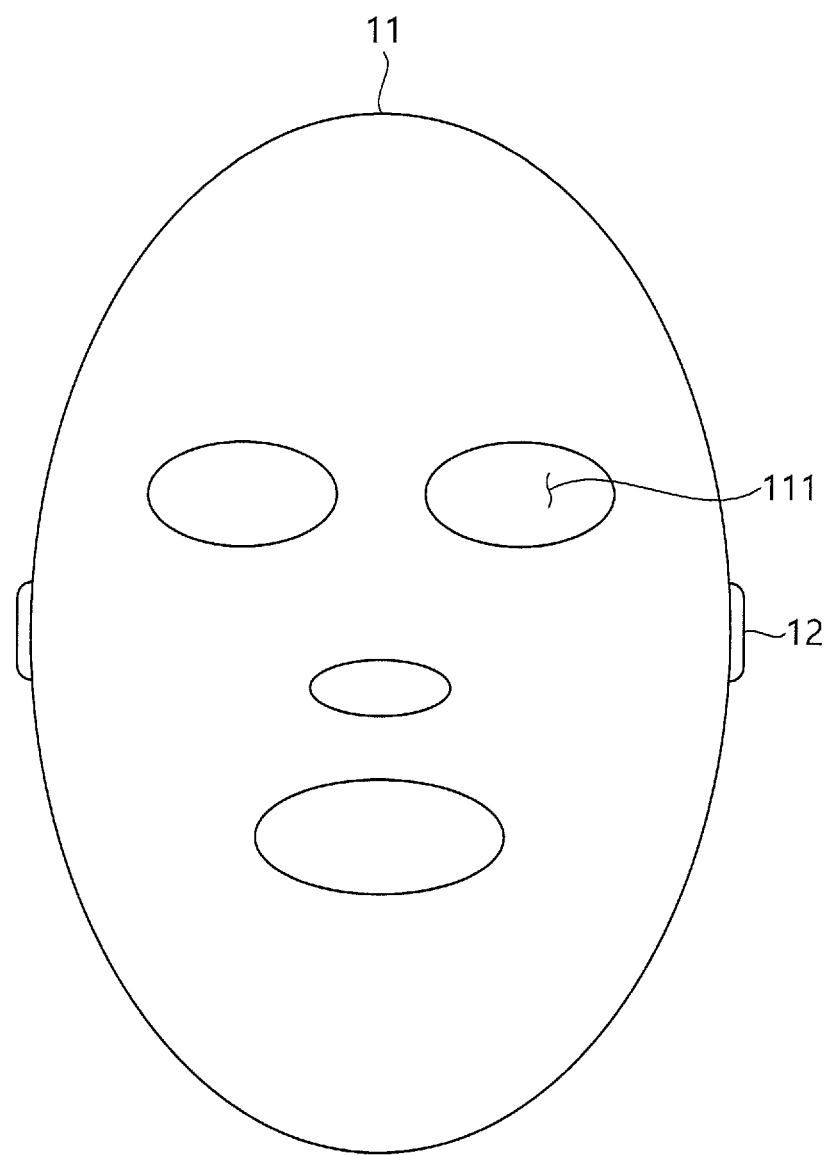
FIG. 3 is a front view of the mask according to the first embodiment of the present invention.
Figure 4:
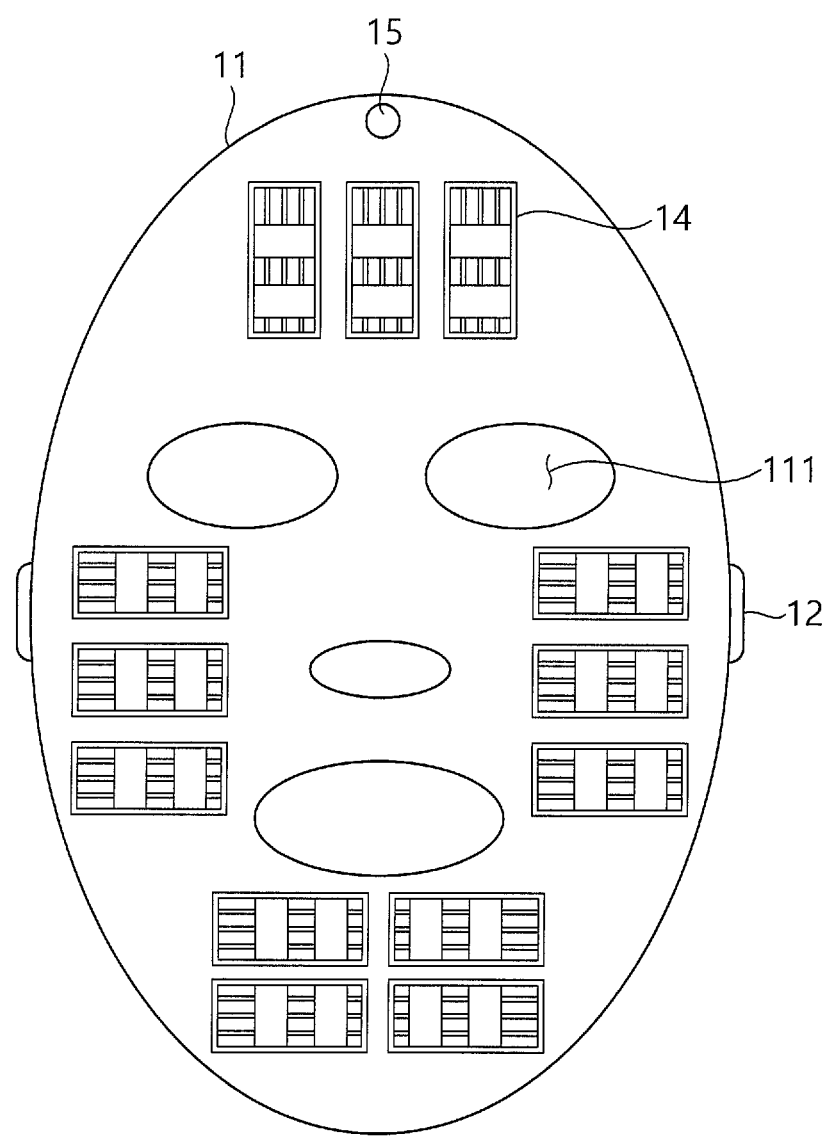
FIG. 4 is a rear view of the mask according to the first embodiment of the present invention.
Figure 5:
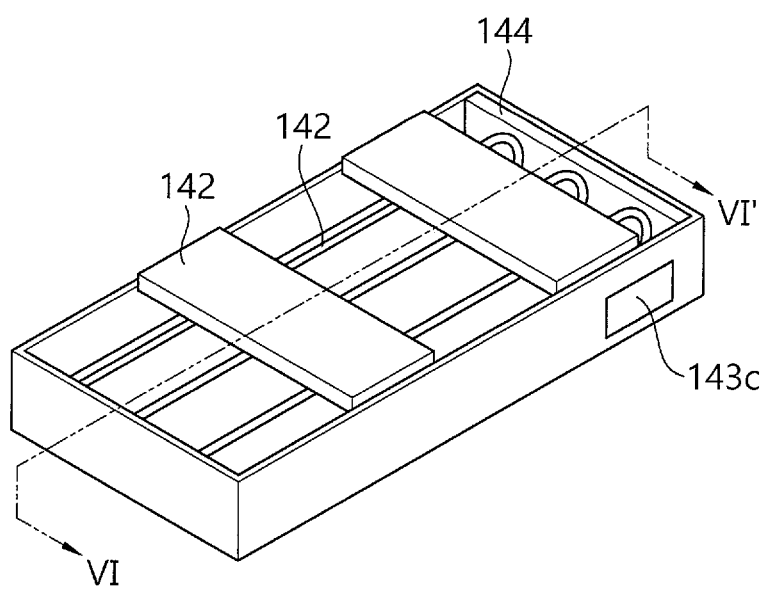
FIG. 5 is a perspective view of a massage unit according to the first embodiment of the present invention.
Figure 6:
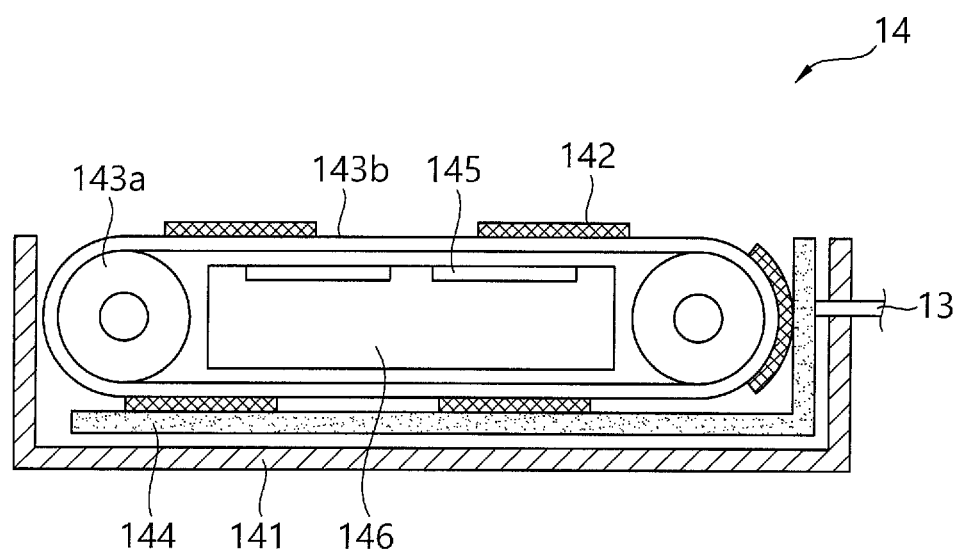
FIG. 6 is a cross-sectional view taken along line VI-VI' of FIG. 5.
Figure 7:
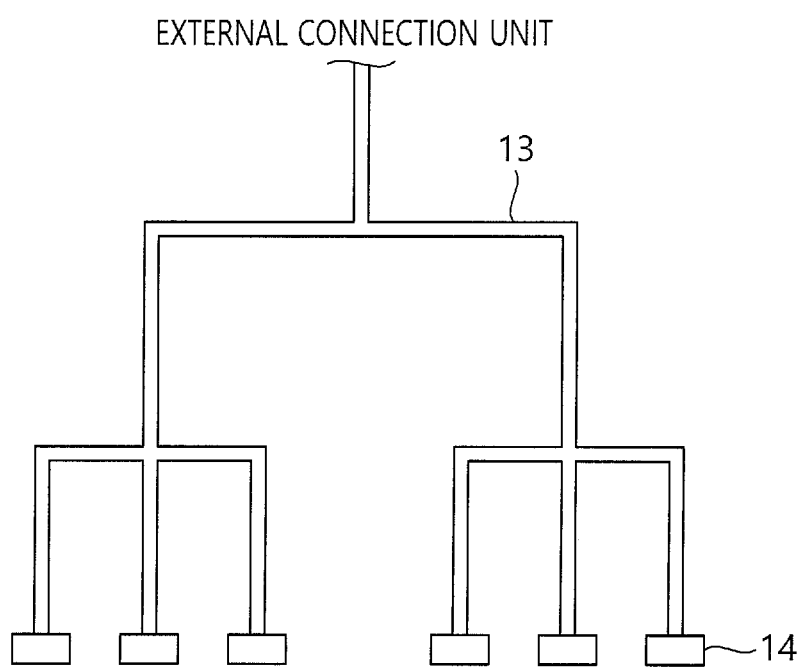
FIG. 7 shows a cosmetics channel according to the first embodiment of the present invention.

FIG. 1 shows the construction of a mask system according to a first embodiment of the present invention, FIG. 2 is a side view of the mask according to the first embodiment of the present invention, FIG. 3 is a front view of the mask according to the first embodiment of the present invention, FIG. 4 is a rear view of the mask according to the first embodiment of the present invention, FIG. 5 is a perspective view of a massage unit according to the first embodiment of the present invention, FIG. 6 is a cross-sectional view taken along line VI-VI' of FIG. 5, and FIG. 7 shows a cosmetics channel according to the first embodiment of the present invention.

A mask system 1 includes a mask 10, a pump 20, a cosmetic container 30, a power supply unit 40 and a control unit 50.

The mask 10 receives cosmetics from the cosmetic container 30 through the pump 20 and the power supply unit 40 supplies power to the mask 10 and the pump 40. The control unit 50 controls the power supply unit 40 to adjust a massage on/off, a massage intensity, massage time, cosmetic supply time, and/or an cosmetic supply amount, etc.

The mask 10 includes a mask body 11, a fixing unit 12, a cosmetic channel 13, a massage unit 14 and an external connection unit 15.

The mask body 11 is provided thicker than a normal mask. The thickness of the mask body 11 is not limited to this, but the thickness of the thickest portion may be 0.5 cm to 5 cm, 0.5 cm to 4 cm, or 1 cm to 3 cm. Openings 111 corresponding to eyes, nose, and mouth are formed in the mask body 11.

In another embodiment, the mask body 11 may be composed of two layers, in which case an internally located layer may be supporting the massage unit 14. In addition, some of the inner part of the mask body 11 may be empty.

The mask body 11 may be made of a plastic material, a silicon material, or the like.

The fixing unit 12 is connected to the side surface of the mask body 11 and serves to closely fix the inner surface of the mask body 11 to the user. The fixing unit 12 can be variously modified as long as the inner surface of the mask body 11 can be closely fixed to the user.

The cosmetic channel 13 communicates with the external connection unit 15 and transfers the cosmetics supplied from the external connection unit 15 to each of the massage units 14. The cosmetic channel 13 may include a tube.

The external connection unit 15 is connected to the cosmetic container 30 through the pump 20 to supply the cosmetics in the cosmetic container 30 to the cosmetic channel 13. The external connection unit 15 may be connected to the pump 20 or the cosmetic container 30 through a one-touch scheme or the like.

A plurality of massage units 14 are provided, but are not limited thereto, and may be arranged to correspond to the user's cheek, forehead and chin. A receiving portion is formed in the mask body 11 to accommodate the massage unit 14.

The massage unit 14 includes a case 141, a massage pad 142, a pad driving part 143, an LED 145, and an LED support 146.

The case 141 is in the shape of a rectangular box with an open top. The inside of the case 141 is connected to the cosmetic channel 13. The case 141 may be made of plastic, but not limited thereto.

The massage pad 142 presses the skin to perform massage. The massage pad 142 may perform massage by directly contacting the skin, or may be provided with a separate member such as a film between the skin and the massage pad 142.

The massage pad 142 may be made of a material having a soft but constant strength, but not limited thereto, and may be made of a silicone rubber material. In addition, the massage pad 142 may be made of a transparent material. The massage pad 142 protrudes outside the case 141, that is, toward the user's face.

The massage pads 142 are provided in the form of a square plate, and five massage pads 142 are used for each massage unit 14. In another embodiment, the massage pad 142 may be circular, polygonal, oval, etc., and may have a pattern of protrusions or the like on its surface. Also, the number of massage pads 142 per massage unit 14 may vary.

The massage pad 142 is moved in one direction by the pad driving part 143 in an endless track manner. Therefore, each of the massage pads 142 moves repeatedly to a position where the skin is pressed and a position where the skin is not pressed, and in the position where the skin is pressed, it is moved in only one direction.

The pad driving part 143 includes rollers 143a, a belt 143b, and a motor 143c. The rollers 143a are positioned at both ends of the belt 143b as a pair. One of the rollers 143a is rotated by the motor 143c. The motor 143c is supplied with power from the power supply unit 40 through a power supply channel (not shown). The position and type of the motor 143c and the like can be variously changed. The massage pad 142 is mounted on the belt 143b and is moved by the rotation of each of the rollers 143a to move the massage pad 142 in one direction. The belt 143b is provided in the form of a string, but in another embodiment, the belt 143b may be provided in a wide band shape.

A cosmetic supply unit 144 is disposed on the inner surface and the lower surface of one side of the case 141 connected to the cosmetic channel 13. The cosmetic supply unit 144 receives cosmetics from the outside through the cosmetic channel 13 and delivers the received cosmetics to the massage pad 142.

In this embodiment, the cosmetic supply unit 144 is provided with a porous material, for example, a foamed foam. The foamed foam may include, but is not limited to, a material of a wet urethane, a dry urethane, a polyether, a polyester, a polyethylene, a silicone, a natural rubber, a nitrile rubber or a polyvinyl alcohol, and a natural porous material may also be used.

The cosmetics supplied through the cosmetic supply unit 144 may be a cleansing agent, a moisturizing agent, a nutrient, and the like.

The LED support 146 is disposed in a space inside the belt 143b between the rollers 143a and the LED 145 is mounted on an upper surface of the LED support 146. The LED 145 is supplied with power from the power supply unit 40 through the power supply channel (not shown).

The LED 145 may apply infrared rays or the like to the user's skin to raise the temperature to thereby improve the massage effect. Further, the LED 145 may apply light in the range of wavelengths of from 600 to 1400 nm which is known to be effective in wrinkle removal and acne treatment or light in the range of wavelengths of from 1400 to 3000 nm which is known to be effected in the enhancement of immunity or collagen generation stimulation, to the skin, but not limited thereto. In addition, the LEDs 145 having different wavelengths may be installed and selected by the user as required.

The installation position of the LED 145 may vary and may be installed in the mask body 11 separately from the massage unit 14.

The cosmetic container 30 accommodates cosmetics and may have various shapes. A plurality of cosmetic containers 30 may be provided, and may be selected by the user as needed.

The power supply unit 40 may be provided in various forms. However, the power supply unit 40 may supply power by being connected to an external power source, supply power using an exchangeable internal battery, or supply power using an internal battery which is connected to an external power source and is rechargeable, but not limited thereto.

The controller 50 can control the on/off, flow rate, and/or operating time of the pump 20. In addition, the control unit 50 can control the massage intensity and/or the massage time of the massage unit 14 and can control the operation time and/or the intensity of the LED 145.

The control unit 50 may have an interface that is easy to use by the user, and may control using by a wired or wireless scheme. The controller 50 may be provided in the form of a remote controller.

Although not shown, the mask 10 further includes a power supply channel for supplying the power of the power supply unit 40 to each of the massage units 14.

Figure 8:
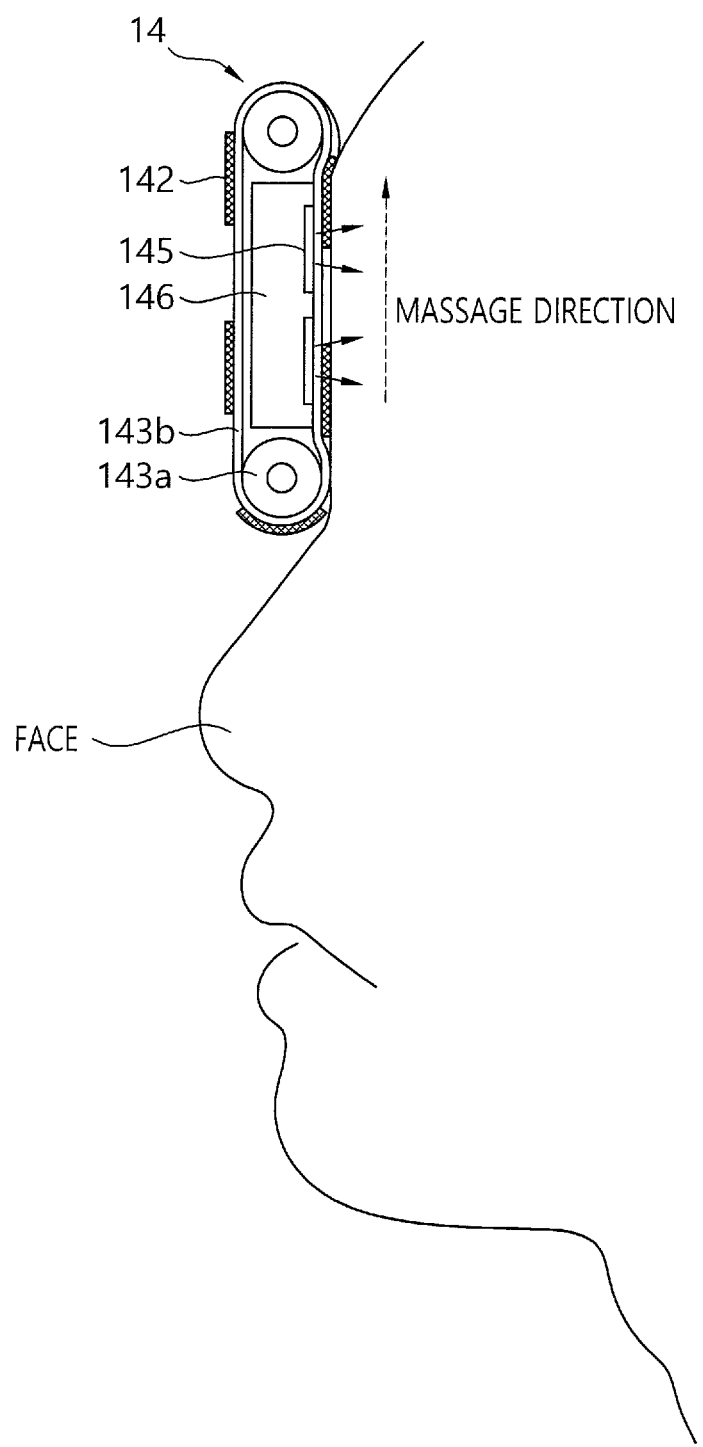
FIG. 8 is a view for explaining the massage function of a massage system according to the first embodiment of the present invention.

The massage function of the mask system 1 described above will be described with reference to FIG. 8.

The user connects the cosmetic container 30 to the external connection unit 15 and wears and fixes the mask 10 on the face. Then, the cosmetic supply and the operation of the massage unit 14 are started through the control unit 50.

The operation of the pad driving part 143 of the massage unit 14 causes the massage pad 142 to massage the skin while moving in one direction in an endless track manner. In this case, the massage direction may be a direction from the center of the face toward the periphery of the face.

When the massage pad 142 passes between the rollers 143a, the massage pad 142 is held in contact with the LED support 146 to maintain a pressing force against the skin.

The LED 145 is also activated to illuminate the user's skin with infrared light to enhance the massage effect. When the massage pad 142 is made light-transmissive, the efficiency of the LED 145 is further improved.

On the other hand, the cosmetics supplied through the cosmetic channel 13 are stored in the cosmetic supply unit 144. The cosmetics stored in the cosmetic supply unit 144 are discharged from the cosmetic supply unit 144 and supplied to the massage pad 142 when the massage pad 142 rotates and comes into close contact with the cosmetic supply unit 144.

Thus, cosmetics are supplied to the surface of the massage pad 142, and when the skin contacts the massage pad 142, the cosmetics are delivered to the skin and the massage is performed.

Figure 9:
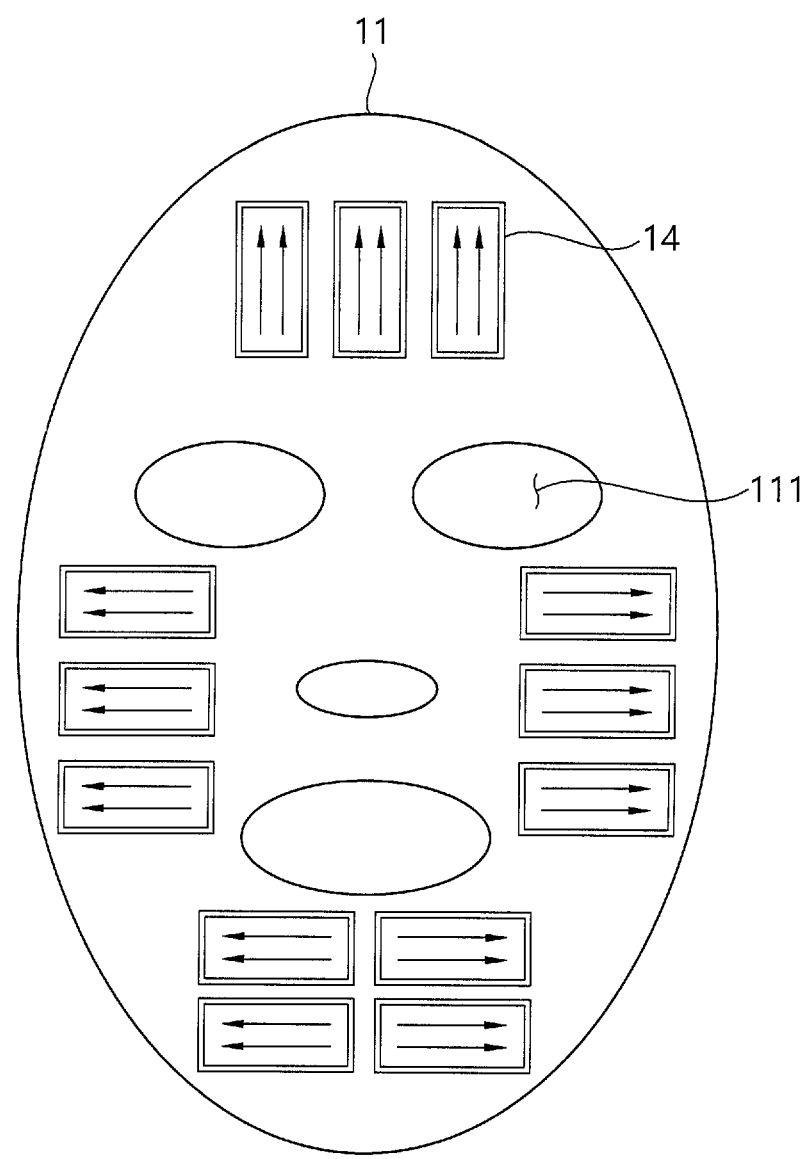
FIG. 9 shows the massage direction in a mask system according to the first embodiment of the present invention.

FIG. 9 shows the massage direction in a mask system according to the first embodiment of the present invention.

The direction of massage performed by each massage unit 14, that is, the direction of movement of the massage pad 142, is the direction in which the massage pad 142 in contact with the skin moves from the center of the face to the periphery of the face. As a result, the massage is performed in such a manner that the wrinkles of the face are spread.

According to the present embodiment described above, since a physical massage can be received through the mask, the satisfaction level of the user is enhanced. When the cosmetics are supplied, the effect of using the conventional mask can be obtained and the effect of the LED light can be obtained as well. In addition, when the massage pad 142 is disposed in a place where wrinkles are likely to be generated on the face, the user can intuitively feel that the wrinkles are improved.

The arrangement of the massage unit 14 may vary, and the size of the massage unit 14 may vary depending on the position.

FIGS. 10 to 13 show massage units according to second to fifth embodiments of the present invention, respectively.

Figure 10:
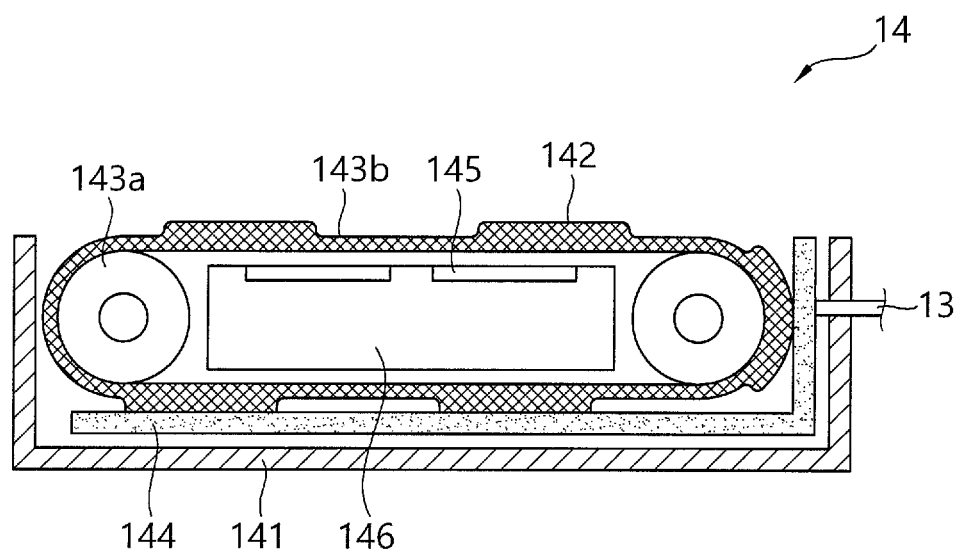
FIGS. 10 to 13 show massage units according to second to fifth embodiments of the present invention, respectively.

In the second embodiment shown in FIG. 10, the massage pad 142 and the belt 143b are integrally formed. In addition, the belt 143b may be in the form of a face (band) rather than a shape of a line.

Figure 11:
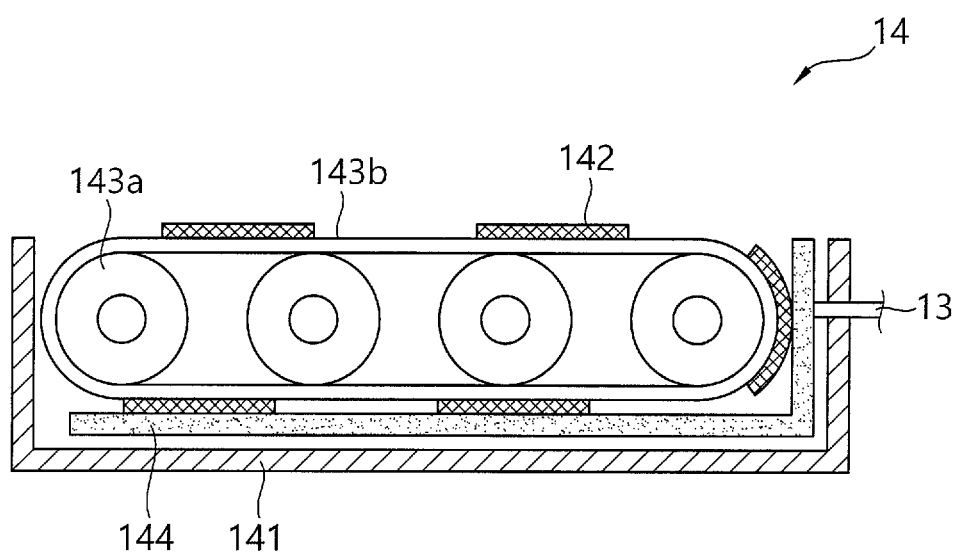

In the third embodiment of FIG. 11, the LED support 146 and the LED 145 are not provided, and four rollers 143a are installed to support the massage pad 142 in the massage process. In the third embodiment, the LED 145 may be installed separately from the massage unit 14.

Figure 12:
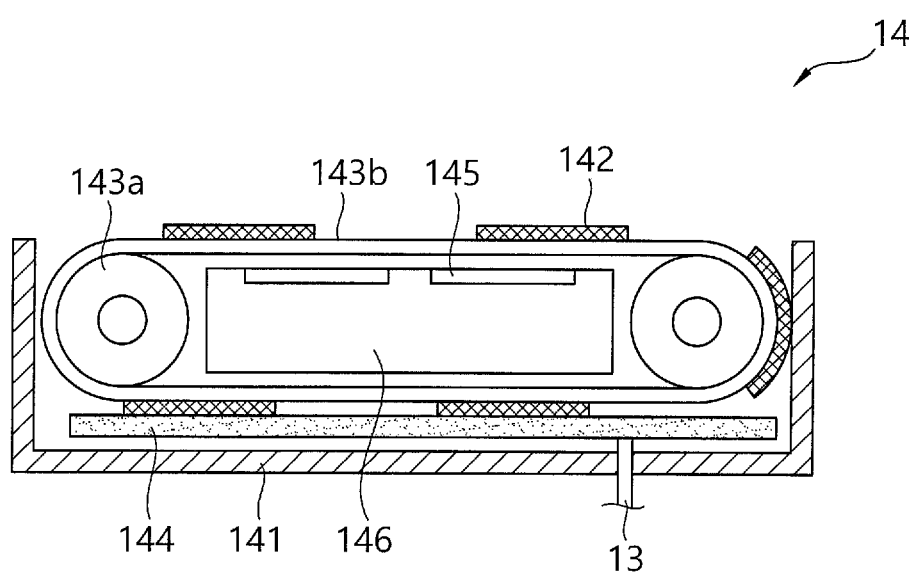

In the fourth embodiment of FIG. 12, the cosmetic channel 13 is connected to the lower surface of the case 141, and the cosmetic supply unit 144 is located only on the lower surface of the case 141. In another embodiment, the cosmetic supply unit 144 may be provided in a protruding shape instead of a sheet shape.

Figure 13:
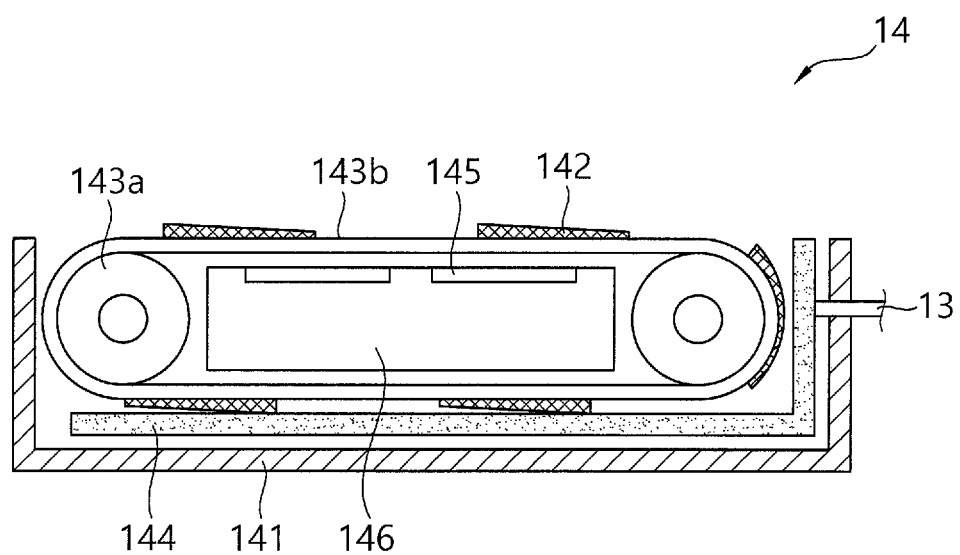

In the fifth embodiment shown in FIG. 13, the thickness of the massage pad 142 becomes thicker toward the direction opposite to the moving direction. According to the fifth embodiment, the user can more clearly feel the massage effect.

The above-described embodiments are illustrative of the present invention, and the present invention is not limited thereto. It will be understood by those skilled in the art that various changes in form and details may be made therein without departing from the spirit and scope of the present invention as defined by the appended claims.

The invention claimed is:

1. A mask having a massage function, the mask comprising:
   a mask body; and
   a massage unit coupled to the mask body,
   wherein the massage unit includes: a massage pad; and a pad driving part for allowing the massage pad to move in one direction while pressing a skin of a user,
   wherein the massage unit further comprises a cosmetic supply unit to supply cosmetics to the massage pad,
   wherein the cosmetic supply unit is formed of materials including a porous material, and
   wherein the cosmetics are discharged from the cosmetic supply unit by a contact between the massage pad and the cosmetic supply unit, to thereby be moved to the massage pad.

2. The mask of claim 1, wherein the massage pad moves in one direction while directly contacting the skin of the user.

3. The mask of claim 1, wherein the pad driving part moves the massage pad in an endless track manner.

4. The mask of claim 3, wherein the pad driving part comprises:
   a belt configured to have the massage pad attached thereon;
   a roller connected to the belt; and
   a motor configured to rotate the roller.

5. The mask of claim 1, further comprising:
   a cosmetic channel configured to receive cosmetics from an external side,
   wherein the cosmetic supply unit receives the cosmetics through the cosmetic channel.

6. The mask of claim 1, wherein the massage unit further comprises a light emitting diode (LED) configured to in-adiate light to the skin of the user.

7. The mask of claim 1, wherein the massage pad massages the skin in a direction of from a center of the user's face toward a periphery of the user's face.

8. The mask of claim 1, further comprising:
   a fixing unit configured to be attached to the mask body and closely fix the mask body to the user's face.

* * * * *